(12) United States Patent
Allen

(10) Patent No.: US 11,633,039 B1
(45) Date of Patent: *Apr. 25, 2023

(54) WASH/SANITATION RACK FOR ATHLETIC EQUIPMENT

(71) Applicant: Sam Allen, Maypearl, TX (US)

(72) Inventor: Sam Allen, Maypearl, TX (US)

(73) Assignee: AIM Design, LLC, Desoto, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/368,186

(22) Filed: Jul. 6, 2021

Related U.S. Application Data

(63) Continuation of application No. 16/793,730, filed on Feb. 18, 2020, now Pat. No. 11,051,614.

(51) Int. Cl.
| | | |
|---|---|---|
| A47B 81/00 | (2006.01) | |
| A47B 96/06 | (2006.01) | |
| A61L 2/04 | (2006.01) | |
| A47B 96/14 | (2006.01) | |

(52) U.S. Cl.
CPC ............. *A47B 81/00* (2013.01); *A47B 96/06* (2013.01); *A47B 96/1441* (2013.01); *A61L 2/04* (2013.01); *A47B 2220/0091* (2013.01)

(58) Field of Classification Search
CPC ..... A47B 81/00; A47B 96/06; A47B 96/1441; A47B 2220/0091; A61L 2/04
See application file for complete search history.

(56) References Cited

U.S. PATENT DOCUMENTS

| | | | |
|---|---|---|---|
| 2,588,529 A | 3/1952 | Hume | |
| 4,102,276 A | 7/1978 | Roveroni | |
| D319,934 S | 9/1991 | Terrell | |
| 6,119,875 A | 9/2000 | Smith | |
| 6,675,978 B2 | 1/2004 | Shea | |
| 7,712,616 B2* | 5/2010 | Barkdoll | A47F 5/0807 211/59.1 |
| D653,462 S | 2/2012 | Trexler | |
| 8,998,009 B2* | 4/2015 | Kim | A47B 96/067 211/175 |
| 9,125,502 B2* | 9/2015 | Gwag | A47F 5/0846 |
| 9,185,984 B2* | 11/2015 | Henke | F16B 7/00 |
| 9,955,782 B2 | 5/2018 | Rue | |
| 10,268,208 B1 | 4/2019 | Hopwood Thomas | |
| 10,420,905 B2* | 9/2019 | Jackson | G09B 23/288 |
| 10,561,242 B1* | 2/2020 | Ignacio | A47B 57/04 |
| D878,831 S | 3/2020 | Rortvedt | |
| 10,799,041 B1* | 10/2020 | Lawson | A47F 5/103 |
| 2002/0117460 A1 | 8/2002 | Crosson | |
| 2013/0153560 A1* | 6/2013 | Lev | H05B 3/342 219/385 |
| 2016/0135594 A1 | 5/2016 | Anderson | |
| 2017/0318961 A1* | 11/2017 | Ramirez | F16B 2/065 |
| 2017/0341923 A1 | 11/2017 | DeWitt | |
| 2017/0342640 A1 | 11/2017 | Stewart | |

OTHER PUBLICATIONS

Office Action dated Oct. 2, 2020 from U.S. Appl. No. 16/793,730.
Amendment dated Dec. 21, 2020 from U.S. Appl. No. 16/793,730.
Notice of Allowance dated Mar. 22, 2021 from U.S. Appl. No. 16/793,730.

* cited by examiner

*Primary Examiner* — Ko H Chan
(74) *Attorney, Agent, or Firm* — James E. Walton

(57) ABSTRACT

A modular wash/sanitation rack assembly having a wall support, a plurality of channels, a gear rack mount, and a gear support. The plurality of channels includes at least two wall support channels.

9 Claims, 8 Drawing Sheets

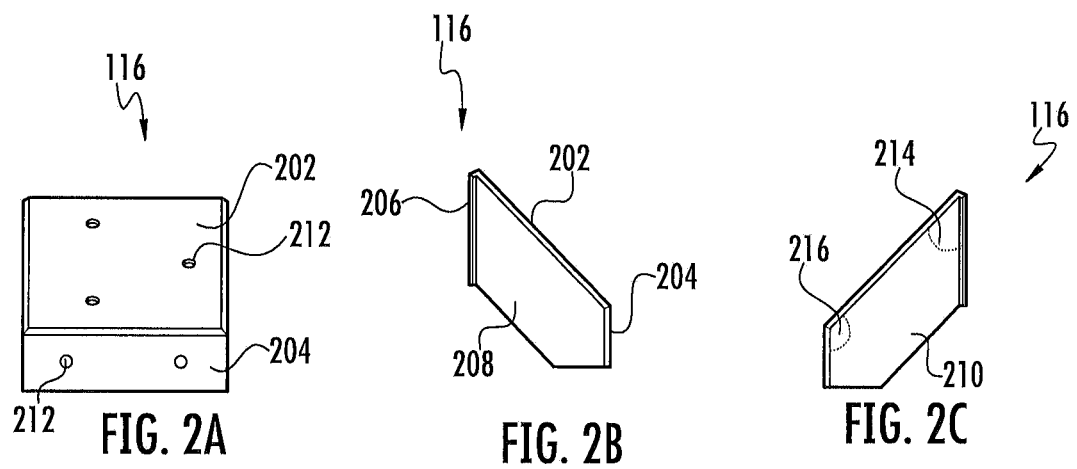
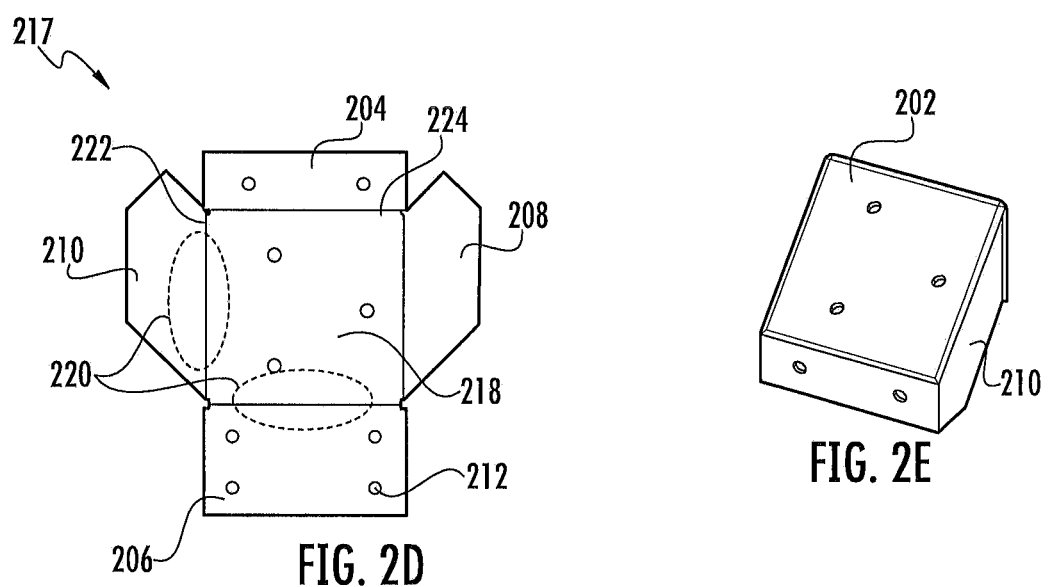

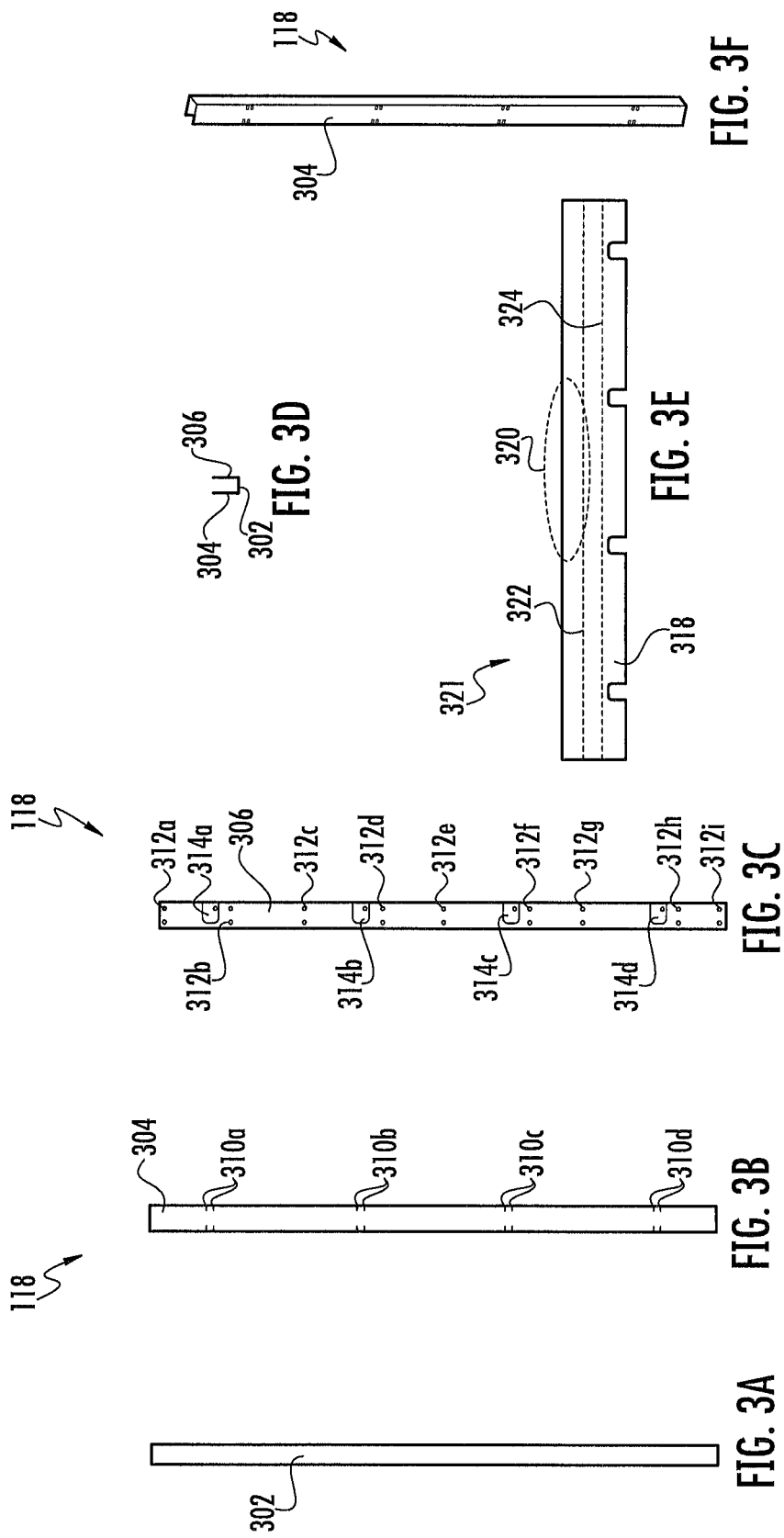

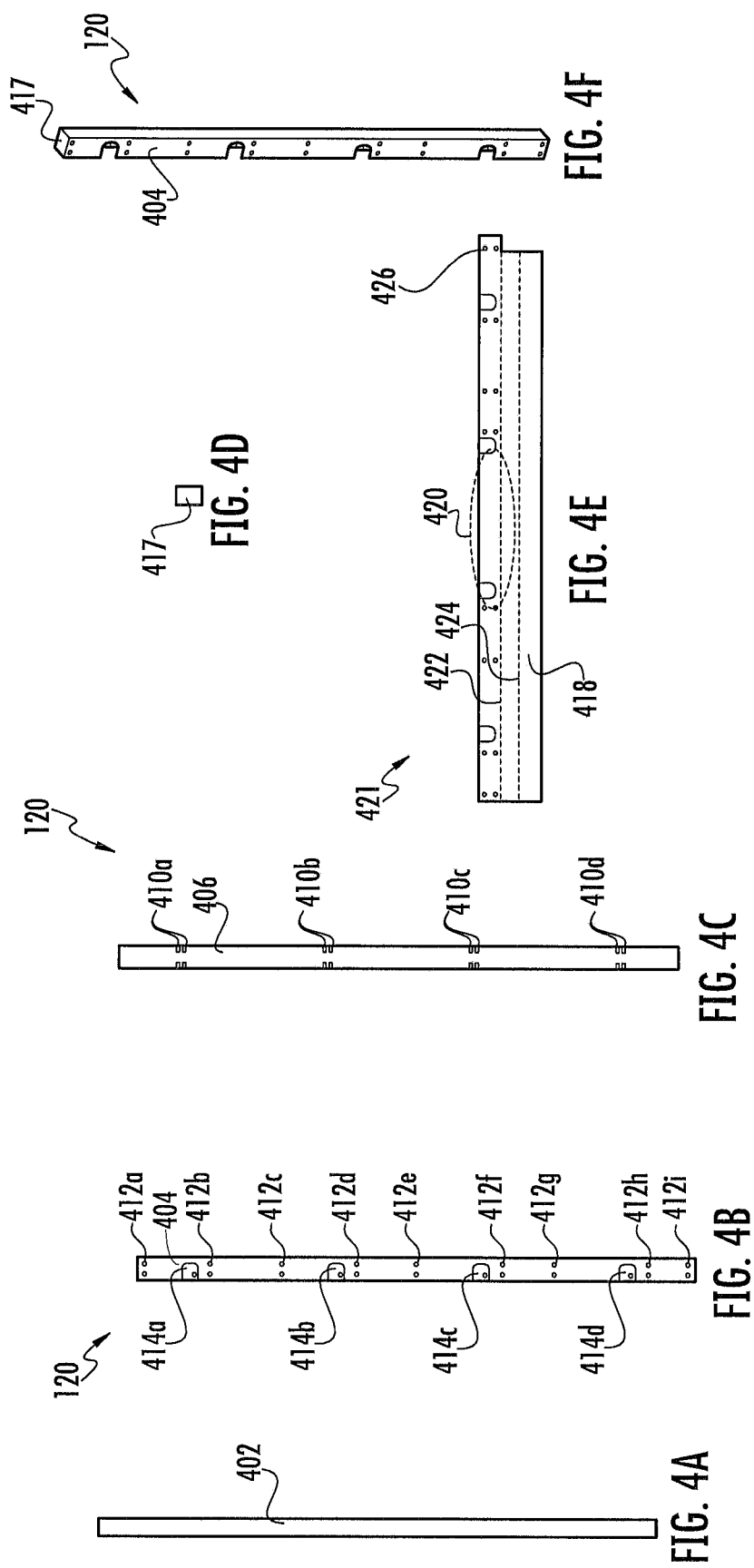

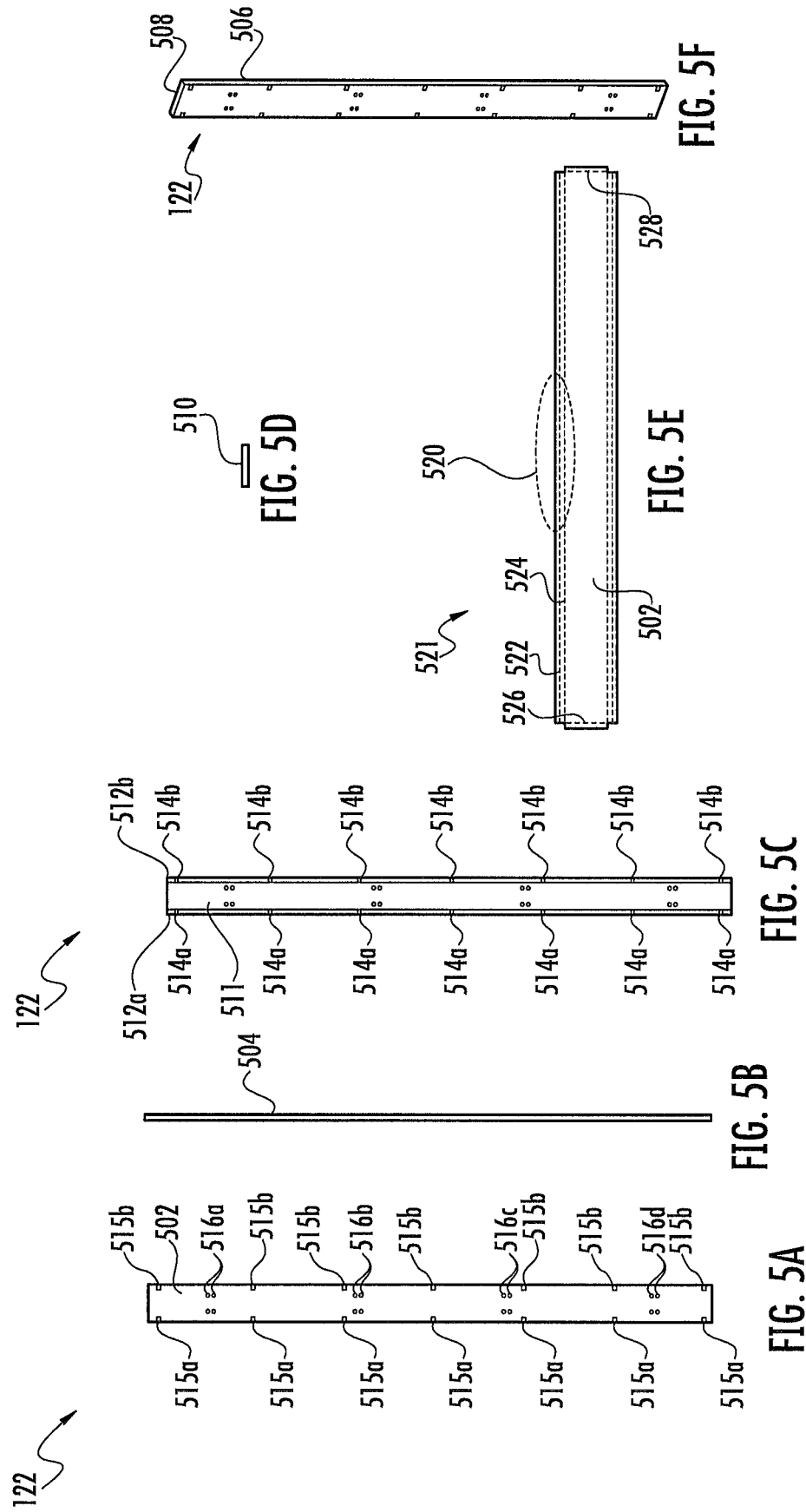

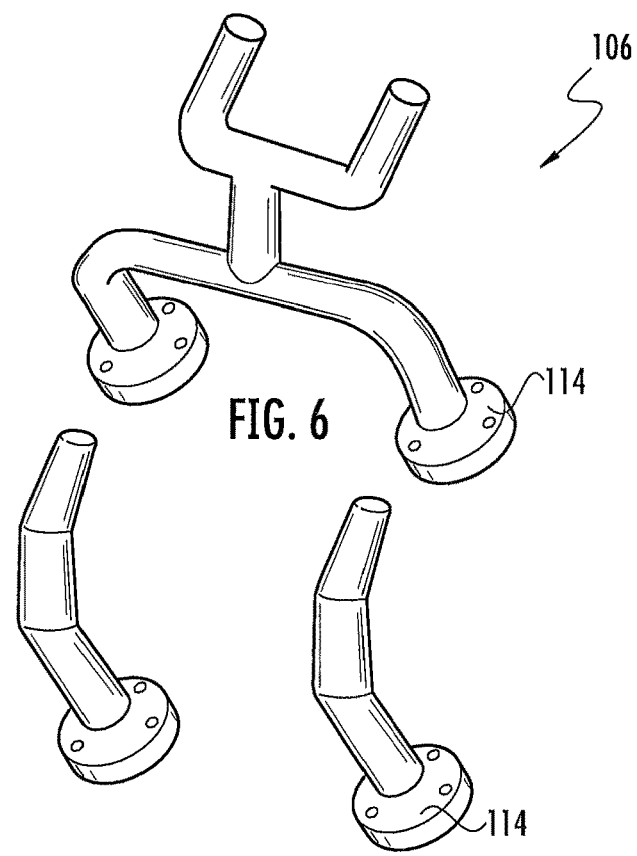
FIG. 6
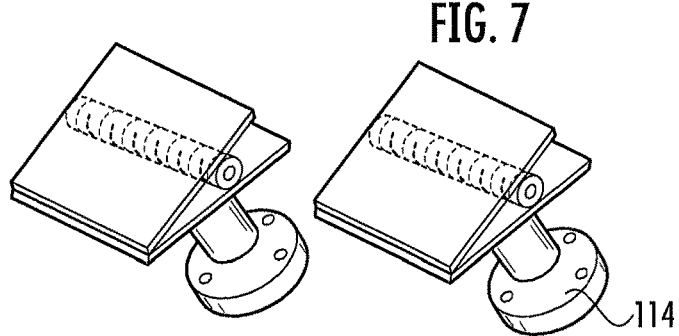
FIG. 7
FIG. 8
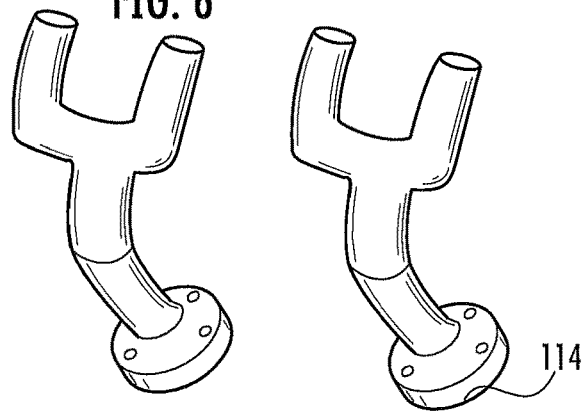
FIG. 9

WASH/SANITATION RACK FOR ATHLETIC EQUIPMENT

This application is a continuation of U.S. patent application Ser. No. 16/793,730, filed 18 Feb. 2020, titled "Wash/Sanitation Rack for Athletic Equipment," which is incorporated herein for all purposes.

BACKGROUND

1. Field of the Invention

The present invention relates in general to the field of equipment racks for athletic gear.

2. Description of Related Art

Racks for athletic gear, school supplies, tools, guns, and for other removable items generally are unstable and made of corrosive materials. If posts, pegs, beams, or bearing members of these racks are stable, they are permanent fixtures, with little or no provision for removing them and customizing storage space. Frequently, these racks are heavy and bulky, requiring mounting prior to door installation, or requiring large equipment/machinery to move them. Fasteners, anchors, sharp corners, or mounting elements often protrude from these racks, presenting a potential hazard to body, equipment, or clothing. Thus, there exists significant room for improvement in the art for overcoming these and other shortcomings of equipment racks.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 2A is a front elevation view of a gear rack mount according to the present application;

FIG. 2B is a side elevation view of a gear rack mount according to the present application;

FIG. 2C is a side elevation view of a gear rack mount according to the present application;

FIG. 2D is a flat pattern view of a gear rack mount according to the present application;

FIG. 2E is a perspective view of a gear rack mount according to the present application;

FIG. 3A is a side elevation view of an inside channel according to the present application;

FIG. 3B is a rear elevation view of an inside channel according to the present application;

FIG. 3C is a front elevation view of an inside channel according to the present application;

FIG. 3D is a top elevation view of an inside channel according to the present application;

FIG. 3E is a flat pattern view of an inside channel according to the present application;

FIG. 3F is a perspective view of an inside channel according to the present application;

FIG. 4A is a side elevation view of an outside channel according to the present application;

FIG. 4B is a front elevation view of an outside channel according to the present application;

FIG. 4C is a rear elevation view of an outside channel according to the present application;

FIG. 4D is a top elevation view of an outside channel according to the present application;

FIG. 4E is a flat pattern view of an outside channel according to the present application;

FIG. 4F is a perspective view of an outside channel according to the present application;

FIG. 5A is a front elevation view of a wall support according to the present application;

FIG. 5B is a side elevation view of a wall support according to the present application;

FIG. 5C is a rear elevation view of a wall support according to the present application;

FIG. 5D is a top elevation view of a wall support according to the present application;

FIG. 5E is a flat pattern view of a wall support according to the present application;

FIG. 5F is a perspective view of a wall support according to the present application;

FIGS. 6 through 9 are perspective views of embodiments of gear supports according to the present application;

Figure 1C:
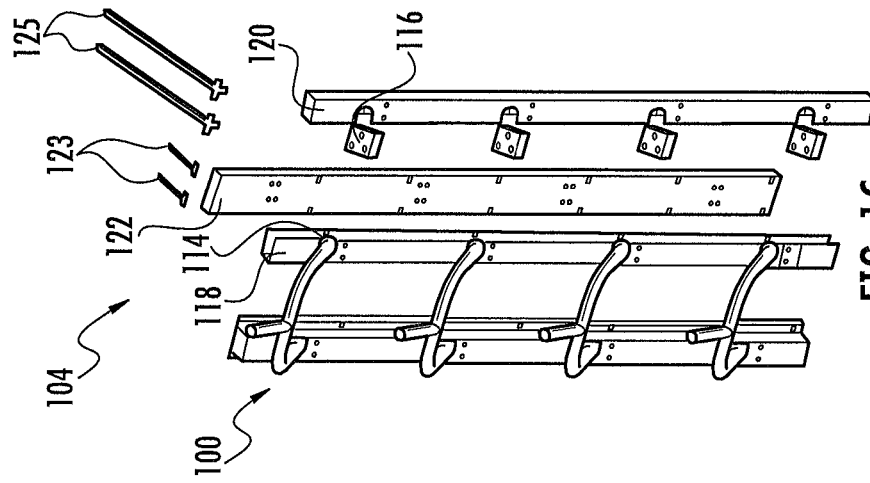
FIG. 1C is a perspective view of an equipment rack assembly according to the present application.

While the assembly of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the wash/sanitation rack for athletic gear are provided below. It will of course be appreciated that in the further development of any embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1B:
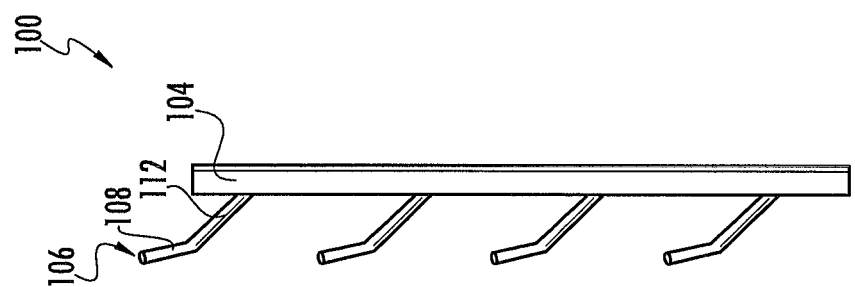
FIG. 1B is a side elevation view of an equipment rack according to the present application.
Figure 1A:
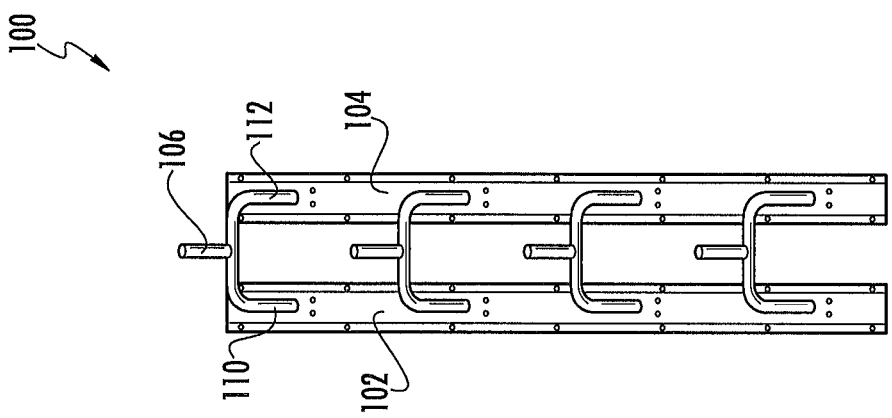
FIG. 1A is a front elevation view of an equipment rack according to the present application.

Referring now to FIGS. 1A and 1B in the drawings, a modular wash/sanitation rack 100 is illustrated. The modular wash/sanitation rack 100, when attached to a wall, is a component of a steam, chemical, high-heat, water, and/or moisturizing wash station. In a preferred embodiment, the wash/sanitation rack 100 includes a left support assembly 102, a right support assembly 104, and a gear support 106. The wash/sanitation rack 100 and its fasteners are made of non-corrosive materials, such as a chromium-nickel alloys, aluminum, tin, brass, copper, nickel, titanium, galvanized steel, and foldable polymer plastics. In a preferred embodiment, the non-corrosive material is stainless steel 301, but other types of steel may be used, such as stainless steel 304.

In a preferred embodiment, the total height to width ratio of the wash/sanitation rack 100 is approximately 5-6. The total height to depth ratio, where depth is the amount the rack protrudes from wall, is approximately 7-8.

It is noted that the terms "left" and "right" are used to refer to respective support assemblies 102, 104 and/or other components described below. Despite this distinctive use, the left and right component parts are generally formed in in a similar or identical manner, except that the parts are formed and/or assembled having an opposite orientation relative to one another.

In a preferred embodiment, the gear support 106 includes a single angled, rounded, centered support beam 108 connected by a left side support 110 and a right side support 112, where the left side support 110 and right side support 112 are flanged, each flange having mounting holes for removable fasteners. In a preferred embodiment, the corners and angles of the gear support 106 are rounded. In other embodiments, the single-beam gear support 106 is interchangeable with different shaped gear supports (FIGS. 6-9). For example, two divided/angled support beams may be attached instead of the depicted single-beam gear support 106.

In a preferred embodiment, the gear support 106 is made from seamless tubing or pipe, bent in the desired shape. In other embodiments, the gear support is made using one or more welds and multiple bends. For example, a seam of the tubing/pipe may be welded and/or a flange may be welded at an end of the tubing/pipe.

In a preferred embodiment, the centered support beam 108 is connected to the left side support 110 and the right side support 112 at an angle to obtain a first slope. The left side support 110 and the right side support 112 are connected respectively to the left support assembly 102 and the right support assembly 104 at another angle to obtain a second slope. In a preferred embodiment, the second slope is greater than the first slope or the second angle is greater than the first angle. For example, the second slope is approximately 55-65% of the first slope. For instance, the angle of the centered support beam is approximately 48-50°, preferably having a slope of about 1.1 to 1.2, and the angle of the side supports 110, 112 is approximately 62-64°, preferably having a slope of about 1.88 to 2.0.

Referring now also to FIG. 1C in the drawings, the perspective view of the wash/sanitation rack 100 includes a partial assembly view of the right support assembly 104 as illustrated. When assembled, the right support assembly 104 includes a beam support flange 114 attached to a gear rack mount 116. The gear rack mount 116 is connected to the inside channel 118. The inside channel 118 is seated within and abuts the outside channel 120. In a preferred embodiment, the front surface of the inside channel 118 connects, or is fastened together, with the front surface of the outside channel 120. The wall support 122 is connected to at least to the rear surface of the outside channel. In a preferred embodiment, the wall support 122 is connected to each of the outside channel 120, the inside channel 118, and the gear rack mount 116 by way of coinciding mounting holes formed in respective surfaces of each of the wall support 122, the outside channel 120, the inside channel 118, and the gear rack mount 116. The wall support 122 is also connected to the wall by way of one or more wall anchors 123 and/or one or more posts 125.

In a preferred embodiment, after assembly of the wash/sanitation rack 100, the wall support 122 is attached to wall anchors 123 to rigidly secure the wash/sanitation rack 100 to a wall (not shown). In a preferred embodiment, the wall to which the wash/sanitation rack 100 is attached is a wall associated with an anterior room of a locker room, such that gear can be removed and hung on the racks for washing and sanitation. For example, locker rooms for college and professional teams often incorporate decorative wood, electronics, fabrics, and other corrosive materials. However, anterior rooms and/or shower stations incorporate cinder block, cement, stainless steel, and other non-corrosive and water-resistant surfaces, where the wash/sanitation rack 100 may be attached. This attachment provides a station for washing and sanitizing gear, such as shoulder pads, helmets, tents, tires, metal bats, shovels, buckets, crosses (i.e., lacrosse sticks), etc. Because the wash/sanitation rack 100 is made from non-corrosive materials, and because wall anchors and fasteners are behind the wall support 122 or other supports, the washing and sanitizing occurs without risk of snags, tears, or rust-staining and coloration. In other embodiments, the fasteners used for assembly are flat-head fasteners and/or the mounting holes incorporate countersinks to minimize fastener exposure. However, flathead fasteners and countersinks are not required due to the overlapping assembly of the components of the wall support 122 and support assemblies 102, 104.

Referring now also to FIGS. 2A through 2C in the drawings, the gear rack mount 116 is illustrated. The gear rack mount 116 includes an angled top surface 202, a front surface 204, a rear surface 206, an angled left side surface 208, and an angled right side surface 210. The angled top surface 202, the front surface 204, and the rear surface 206 each includes a set of mounting holes 212. The angles of the angled side surface 208 and the angled right side surface 210 are supplementary angles. For example, the first angle 214 is a 45° angle, and the second angle 216 is a 135° angle. It is noted that other supplementary angle combinations are encompassed by the present application.

Referring now also to FIG. 2D in the drawings, a flat pattern 217 of the gear rack mount 116 is illustrated. The flat pattern 217 is made from a single sheet of material and includes a bottom surface 218, indicia 220, such as bend/fold directions, a longitudinal bend line 222, and a lateral bend line 224. It is noted that flat pattern 217 ships and stores easier than pre-formed gear rack mounts. In other embodiments, a pre-formed gear rack mount, a solid 3D gear rack mount, or a gear rack mount welded from multiple pieces connected together in the form of gear rack mount 116 is also encompassed by the present application.

Referring now also to FIG. 2E in the drawings, after folding or bending along bend lines, a three-dimensional gear rack mount 116 takes form. The 3D form is connected between a flange of the gear support 106 and the inside channel 118.

Referring now also to FIGS. 3A through 3D in the drawings, the inside channel 118 is illustrated. The inside channel 118 includes a right side surface 302, a rear surface 304, and a front surface 306. The rear surface 304 includes multiple sets 310 of mounting holes. For example, in a preferred embodiment, the rear surface 304 includes a first set 310a, a second set 310b, a third set 310c, and a fourth set 310d. In a preferred embodiment, the number of sets 310 corresponds to the number of gear supports 106 attached to the wash/sanitation rack 100. In other embodiments, the number of sets 310 of holes corresponds to a number of gear rack mount placement options included on the inside channel. The front surface 306 includes multiple sets 312 of mounting holes for attachment with the front surface of the outside channel 120. For example, the front surface of the inside channel 118 includes nine sets of mounting holes, 312a, 312b, 312c, 312d, 312e, 312f, 312g, 312h, and 312i. It is noted that additional numbers of sets of mounting holes, placement options, and combinations thereof are encompassed by the present application.

In a preferred embodiment, the front surface 306 includes a set of cutouts 314, or removed material portions, to slide around and abut a side support 110, 112 of the gear support 106. The number cutouts within the set of cutouts 314 corresponds to the number of gear supports 106 included with the assembly. In a preferred embodiment, there are at least four cutouts 314a, 314b, 314c, and 314d in the set of cutouts. In other embodiments, there is at least one cutout 314 to correspond to at least one gear support 106.

Referring now also to FIG. 3E in the drawings, a flat pattern 321 of the left side inside channel 118 is illustrated. The flat pattern 321 is made from a single sheet of material and includes an inside surface 318, indicia 320, such as bend/fold directions, a first longitudinal bend line 322, and a second longitudinal bend line 324.

Referring now also to FIG. 3F in the drawings, after folding or bending along bend lines 322 and 324, a three-dimensional inside channel 118 takes form. The 3D form is connected to a flange of the gear support 106 and is seated within the outside channel 120.

Referring now also to FIGS. 4A through 4D in the drawings, the outside channel 120 is illustrated. The outside channel 120 includes a side surface 402, a front surface 404, a rear surface 406, and a top surface 417. The rear surface 406 includes multiple sets 410 of mounting holes. For example, in a preferred embodiment, the rear surface 406 includes a first set 410a, a second set 410b, a third set 410c, and a fourth set 410d. In a preferred embodiment, the number of sets 410 corresponds to the number of gear supports 106 attached to the wash/sanitation rack 100. In other embodiments, the number of sets 410 of holes corresponds to a number of gear rack mount placement options. The front surface 404 of the outside channel 120 includes nine sets of mounting holes, 412a, 412b, 412c, 412d, 412e, 412f, 412g, 412h, and 412i for attachment or connection with the front surface of the inside channel 118. It is noted that additional numbers of sets of mounting holes, placement options, and combinations thereof are encompassed by the present application. In other embodiments, the additional sets of holes that are not used for placing gear mount racks are used to more securely connect the inside channel with the outside channel 120 or with the wall support 122.

In a preferred embodiment, the front surface 404 includes a set of cutouts 414, or removed material portions, to slide around and abut a side support 110, 112 of the gear support 106. The number cutouts within the set of cutouts 414 corresponds to the number of gear supports 106 included with the assembly. In a preferred embodiment, there are at least four cutouts 414a, 414b, 414c, and 414d in the set of cutouts. In other embodiments, there is at least one cutout 414 to correspond to at least one gear support 106.

Referring now also to FIG. 4E in the drawings, a flat pattern 421 of the left side outside channel 120 is illustrated. The flat pattern 421 is made from a single sheet of material and includes an inside surface 418, indicia 420, such as bend/fold directions, a first longitudinal bend line 422, a second longitudinal bend line 424, and a lateral bend line 426.

Referring now also to FIG. 4F in the drawings, after folding or bending along bend lines 422, 424, and 426, a three-dimensional outside channel 120 takes form. The 3D form is connected to, or houses, the inside channel 118 and is further connected to the wall support 122.

Referring now also to FIGS. 5A through 5D in the drawings, the wall support 122 is illustrated. The wall support 122 includes a front surface 502, a left side surface 504, a right side surface 506, a top surface 508, a bottom surface 510, and a rear surface 511. The rear surface 511 includes at least a left side mounting channel 512a and a right side mounting channel 512b. Each mounting channel 512a and 512b includes a set 514 of mounting holes. For example, in a preferred embodiment, the rear surface 511 includes two mounting channels 512, where the first mounting channel has a first set 514a of mounting holes, and the second mounting channel has a second set 514b of mounting holes. In a preferred embodiment, the number of holes in a set 514 corresponds to the number of wall anchors desired to attach the wash/sanitation rack 100 to a wall. The number of anchors may vary depending on the weight of gear, the type of wall, a thickness of the wash/sanitation rack 100, a type of wall anchors used, or a combination of these and similar factors. In other embodiments, the number of holes in a set 514 corresponds to a number of gear supports 106 to be attached. For example, the greater the number of gear supports 106 attached, the greater the number of holes in the sets 514. In at least one embodiment, the sets of holes 514 are used for posts 125 that extend out the back of the wash/sanitation rack 100.

In a preferred embodiment, the front surface 502 includes one or more sets of access holes 515. The number of sets of access holes 515 will correspond to the number of channels 512 formed in the back surface of the wall support 122. In a preferred embodiment, the front surface 502 includes two sets of access holes 515a and 515b. In a preferred embodiment, a diameter of the access holes 515 is larger than a diameter of the mounting holes 514 in the channels 512 of the wall support 122. The larger diameter allows tool access, such as a bit or screwdriver head, to the wall anchors 123 behind the wall support 122. In other embodiments, the diameter of the access holes 515 is equivalent to the diameter of the mounting holes 514 in the channels 512. In these embodiments, the wall anchors 123 or posts 125 are inserted through the front surface 502 and the channels 512, with a head of the anchors 123 or posts 125 abutting the front surface 502 of the wall support 122.

In a preferred embodiment, the front surface 502 includes multiple sets 516 of mounting holes. For example, in a preferred embodiment, the front surface 502 includes a first set 516a, a second set 516b, a third set 516c, and a fourth set 516d. In a preferred embodiment, the number of sets 516 corresponds to the number of gear supports 106 attached to the wash/sanitation rack 100. In other embodiments, the number of sets 516 of holes corresponds to a number of gear rack mount placement options. Although the configuration of four gear supports 106 requires only four sets 516 of holes, additional sets of holes may be added for different placement options for gear rack mounts 116, and thereby placement options for gear supports 106. It is noted that additional sets 514 of holes (not shown) may also be formed in the rear surface 511. It is further noted that additional numbers of sets of mounting holes, placement options, and combinations thereof are encompassed by the present application. In other embodiments, the additional sets of holes that are not used for placing gear mount racks are used to more securely connect the wall support 122 to the wall.

Referring now also to FIG. 5E in the drawings, a flat pattern 521 of the wall support 122 is illustrated. The flat pattern 521 is made from a single sheet of material and includes the front surface 502, indicia 520, such as bend/fold directions, a first longitudinal bend line 522, a second longitudinal bend line 524, a first lateral bend line 526, and a second lateral bend line 528.

Referring now also to FIG. 5F in the drawings, after folding or bending along bend lines 522, 524, 526, and 528, a three-dimensional wall support 122 takes form. The 3D form is connected to the outside channel 120 and is further connected to the wall. In other embodiments, one or more fasteners extend from the wall support through each of the outside channel 120, the inside channel 118, the gear rack mount 116, and finally to a flange of the gear support 106 to secure each component part together.

Referring now also to FIGS. 6 through 9 in the drawings, multiple interchangeable gear supports 106 are illustrated. The interchangeable gear supports 106 include multiple beams formed as a single fork shape, single separated beams, spring-biased clamps, and multiple beams formed as separate forks. It is noted that different combinations (shown and not shown) of interchangeable gear supports 106 are encompassed by the inventive concepts of the present application.

Figure 10A:
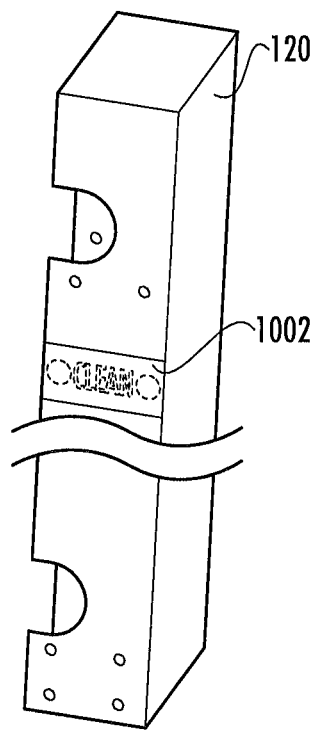
FIGS. 10A through 10B are perspective partial views of a rack support having a heat/sanitation indicator according to the present application.
Figure 10B:
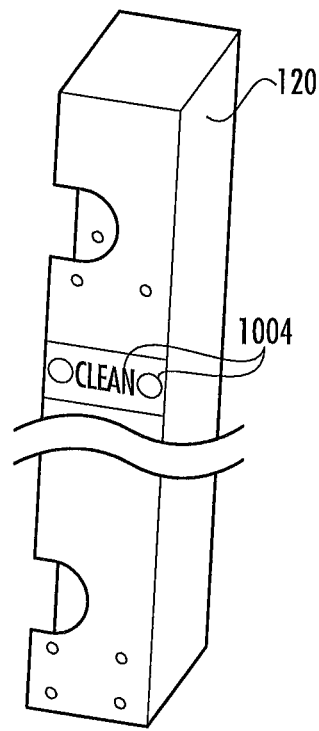
Figure 10C:
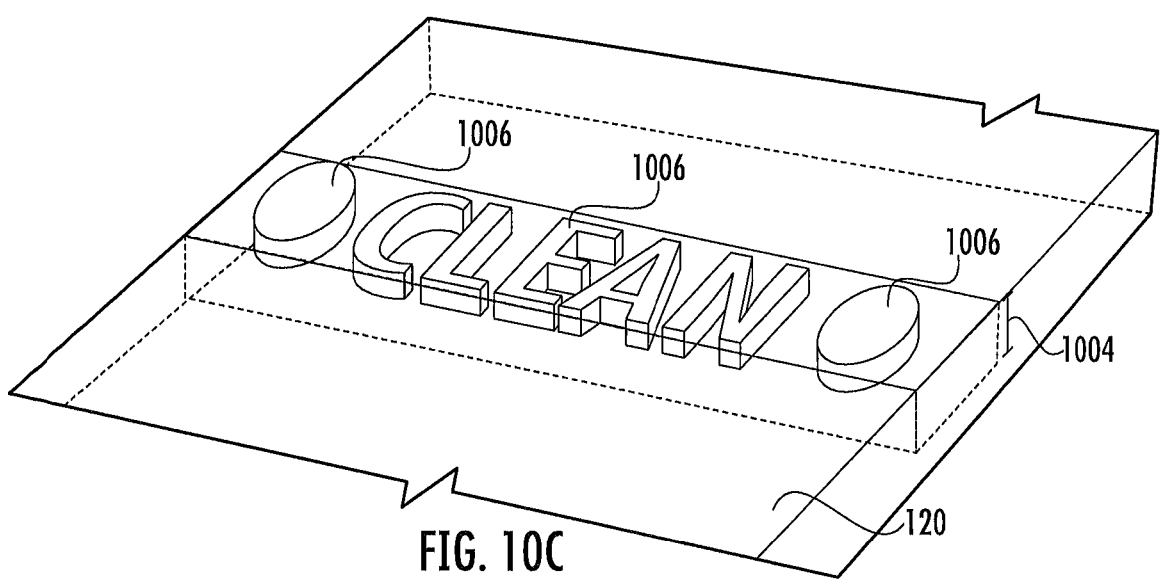
FIG. 10C is a perspective partial view of a facial surface of a wash/sanitation rack support with a heat/sanitation indicator according to the present application.

Referring now also to FIGS. 10A and 10B in the drawings, a heat or sanitation indicator 1002 is illustrated. The indicator 1002 is formed in a facial surface of a beam or a channel and is used to indicate when an appropriate temperature threshold is reached. When the appropriate temperature threshold has been reached and/or maintained for a desired amount of time, the gear that is being washed/sanitized is known to be substantially clean. For example, the heat/sanitation indicator 1002 is formed on the facial surface of the outside channel 120, as depicted in FIG. 10A. When the desired temperature is reached and/or maintained, a color-changing portion 1004 of the indicator changes color to indicate that the temperature threshold has been reached/maintained.

In a preferred embodiment, the heat/sanitation indicator 1002 is formed by cutting a depth 1004 into the facial surface of the outside channel 120 and filling the depth 1004 with a temperature color-changing material. It is noted that although the heat/sanitation indicator 1002 is depicted as formed on the facial surface of the outside channel 120, any facial surface of a support of the wash/sanitation rack 100 may have a heat/sanitation indicator formed or placed thereon. It is further noted that although cutting is described as the method of forming the heat/sanitation indicator 1002, other forms, such as etching, engraving, laser engraving, laser cutting, and combinations thereof may be used to form the indicator depressions.

In a preferred embodiment, the depth 1004 may be formed as one or more indicia and/or symbols 1006. The depth 1004 is filled with a temperature-indicating substance, such as a solvent, and one or more suitable moieties or constituents, such as pigments, dyes, or colorants, and then sealed with a clear sealant. For example, a solvent may including ortho-bromonitrobenzene:ortho-chloronitrobenzene (75:25), and a suitable constituent may include pinacyanol iodide (at 0.035 wt. %). For a list of potential solvents and constituents, see U.S. Pat. No. 4,232,552, which is incorporated by reference in its entirety. In other embodiments, a waterproof or water resistant temperature indicator tape or adhesive strip, such as cellulose acetate, vinyl plastic, flexible butyl tape, or combinations thereof, is used in lieu of cutout and filled indicators.

In at least one embodiment, the depth 1004 extends through the entire width of the wall support forming a perforation. Multiple perforations may be placed along a surface of the wall support to provide air flow to the wash/sanitation rack 100. In this embodiment, the wash/sanitation rack 100 is connected to a heating and/or cooling air source. For example, the air source may be internal, such as a blower or fan housed within a portion of the wall support. By way of another example, the air source may be external, such as with ductwork connecting the wash/sanitation rack 100 with an HVAC system 1106. The shape, dimensions, and/or orientations of the perforations may vary depending on a desired function of the airflow. For example, perforations 1104 may be square, round, oval, symmetrical, non-symmetrical, indicia-shaped, protruding, or indented. By way of another example, the perforations 1104 may be smaller near the inlet connecting the wall support to the air source, and may be gradually larger further from the inlet associated with the air source, more evenly dispersing the air flow than if the perforations were all of the same dimension and size despite how they are located relative to the air source. By way of yet another example, the perforations may be smaller or have an outward bevel with perforations near any electrical equipment, such as a fan or blower, in order to prevent liquids from entering the perforations and interfering with the electrical operation of the fan or blower.

In a preferred embodiment, the wall support 122 is anchored by wall anchors 123 to a wall of an anterior room of a locker room. In other embodiments, once the gear support 106, gear rack mount 116, inside channel 118, outside channel 120, and wall support 122 are all securely connected together, the assembly forms a single unit with posts 125 protruding out the back of the assembly, which as a unit may be moved (i.e., without requiring disassembly of the individual parts) to different holes in a wall. For example, small-scale pegs or peg units of a peg board may be lifted in order to remove the weight on posts protruding out the back of the peg unit. This allows the user to remove the unit from the peg board or move the unit to a different set of holes on the peg board. A similar result occurs in embodiments where the rack assembly is secured together with posts 125 protruding out of the back of the assembly. The posts 125 are inserted into the same or different holes of the wall in order to re-mount the wash/sanitation rack 100.

The hollows created by using 3D forms created by bending or folding flat patterns results a significant weight reduction in the assembled wash/sanitation rack 100. The use of stainless steel, or other high-strength and non-corrosive materials, for sheet metal, flat patterns, and/or fasteners results a structurally sound, high-weight bearing, rust-resistant support for the rack. Incorporating thermometers or other temperature indicators into the support surfaces provides operators with an indication of when equipment is sanitized.

Figure 11:
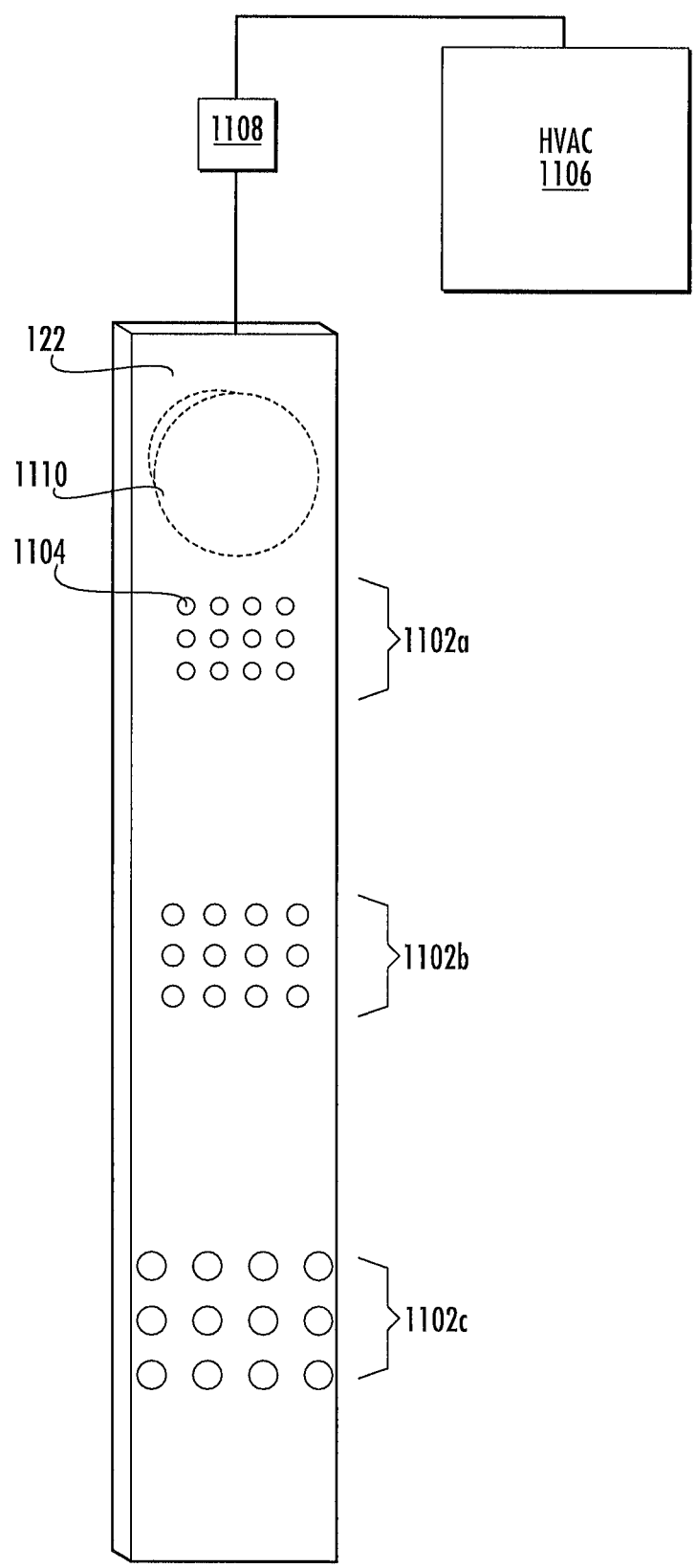
FIG. 11 is an elevation plan view of a perforated wall support, air source, and air source connector according to the present application.

Referring now also to FIG. 11 in the drawings, an embodiment of a wall support 122 having one or more groups 1102 of perforations 1104 is illustrated. A group 1102 may be associated with a position of a gear support 106. For example, a first group 1102a is positioned relative, such as above, below, or in-line, with a first gear support 106; a second group 1102b is positioned relative to a second gear support 106; and a third group 1102c is positioned relative to a third gear support 106. In a preferred embodiment, the wall support 122 is connected to an external air source 1106 by way of a connector 1108. The connector 1108 includes an airway grommet, a right-angle duct, a curved duct, a gasket, a weld, or combinations thereof. In other embodiments, the wall support is connected to an internal air source 1110, such as a centrifugal blower, a high-speed blower, or a regenerative impeller blower.

In a preferred embodiment, a size, shape, or dimension of the perforations 1104, or groups of perforations 1102 vary depending on multiple factors, such as a location of the air source connector 1108 (bottom and/or top of wall support 122), a configuration and number of the gear supports 106 attached to the wall support 122, a type of air source used (internal and/or external), and an intended use of the wash/sanitation rack 100.

It is noted that although FIG. 11 depicts perforations 1104 formed in wall support 122, other supports or components of the wash/sanitation rack 100 may include perforations 1104. For example, gear supports 106 may include one or more perforations 1104 or one or more groups 1102 of perforations. It is further noted, that embodiments that incorporate an air source may have sides, edges, and connectors sealed using welds, threads, gaskets, and other sealing means known in the art.

It is apparent that an assembly with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

I claim:

1. A modular wash/sanitation rack assembly, comprising:
   a plurality of wall supports;
   a plurality of support assemblies, each support assembly comprising:
     a support flange;
     a support channel comprising:
       an outside channel; and
       an inside channel disposed within and abutting the outside channel; and
     a gear rack mount disposed within the support channel; and
   a plurality of gear supports, at least one of the gear supports comprising a first set of mounting holes; and
   a second set of mounting holes on the gear rack mount;
   wherein the second set of mounting holes corresponds to the first set of mounting holes, such that at least one of the gear supports is coupled to the gear rack mount.

2. The A modular wash/sanitation rack assembly of claim 1, comprising:
   a plurality of wall supports
   a plurality of support assemblies, each support assembly comprising:
     a support flange;
     a support channel comprising:
       an outside channel; and
       an inside channel disposed within and abutting the outside channel; and
     a gear rack mount disposed within the support channel; and
   a gear support coupled to the gear rack mount;
   wherein at least one of the support channels, the gear rack mount, and the plurality of wall supports comprises:
   a flat pattern folded into a three-dimensional (3D) form, the flat pattern further comprising:
     bend lines on the flat pattern; and
     indicia formed or placed on the flat pattern.

3. The wash/sanitation rack assembly of claim 1, wherein at least one of the gear supports comprises:
   an angled support beam; and
   an angled side support connected to the angled support beam.

4. The A modular wash/sanitation rack assembly of claim 1, comprising:
   a plurality of wall supports;
   a plurality of support assemblies, each support assembly comprising:
     a support flange;
     a support channel comprising:
       an outside channel; and
       an inside channel disposed within and abutting the outside channel; and
     a gear rack mount disposed within the support channel, the gear rack mount comprising:
       an angled top surface;
       a front surface;
       a rear surface;
       a first angled side surface;
       a second angled side surface; and
       a plurality of mounting holes; and
   a gear support coupled to the gear rack mount.

5. The A modular wash/sanitation rack assembly of claim 1, comprising:
   a plurality of wall supports;
   a plurality of support assemblies, each support assembly comprising:
     a support flange;
     a support channel comprising:
       an outside channel; and
       an inside channel disposed within and abutting the outside channel;
       wherein the inside channel includes a first front surface and a first rear surface;
       wherein the outside channel includes a second front surface and a second rear surface;
       wherein the first front surface and the second front surface each include a set of mounting holes and a set of cutouts; and
       wherein the first rear surface and the second rear surface each include a set of mounting holes' and
     a gear rack mount disposed within the support channel; and
   a gear support coupled to the gear rack mount.

6. The wash/sanitation rack assembly of claim 1, wherein the plurality of wall supports and the plurality of gear supports comprise a non-corrosive material.

7. The wash/sanitation rack assembly of claim 1, wherein the plurality of wall supports further comprises:
   a facial surface, the facial surface having a heat/sanitation temperature indicator.

8. The wash/sanitation rack assembly of claim 1, wherein the gear rack mount is significantly hidden from external view.

9. The wash/sanitation rack assembly of claim 1, wherein the plurality of wall supports, the inside channel, the outside channel, and the gear rack mount include coinciding mounting holes, configured such that a single fastener can be used to secure a portion of a single wall support to a portion of a single support assembly.

\* \* \* \* \*